United States Patent [19]
Birkel et al.

[11] Patent Number: 5,425,468
[45] Date of Patent: Jun. 20, 1995

[54] MULTI-PURPOSE SECRETION RECEPTACLE

[76] Inventors: Dianne B. Birkel, 5315 W. County Line Rd., Brown Deer, Wis. 53223; Kim V. Povlick, 7800 W. Abott Ave., Greendale, Wis. 53129

[21] Appl. No.: 23,569

[22] Filed: Feb. 26, 1993

[51] Int. Cl.6 .............................................. B65D 90/04
[52] U.S. Cl. .................................... 220/404; 220/908; 383/11; 383/33; 604/317
[58] Field of Search ................... 220/403, 404, 908; 383/11, 33; 128/849, 852, 853, 854; 604/317

[56] References Cited

U.S. PATENT DOCUMENTS

| | | |
|---|---|---|
| 387,622 | 8/1888 | Clench . |
| 783,971 | 1/1905 | Meinecke et al. . |
| 2,228,111 | 1/1941 | Hamilton . |
| 3,148,799 | 9/1964 | Meroney ............................ 220/404 |
| 3,321,070 | 5/1967 | Childs . |
| 3,346,883 | 10/1967 | Ersek ............................ 383/33 X |
| 3,514,012 | 5/1970 | Martin ............................ 220/404 |
| 4,747,701 | 5/1988 | Perkins ............................ 383/33 |
| 4,822,178 | 4/1989 | Taylor ............................ 383/33 |
| 4,948,266 | 8/1990 | Bencic ............................ 220/404 X |
| 4,969,596 | 11/1990 | Schulbaumm . |
| 5,018,637 | 5/1991 | Miller ............................ 220/404 |
| 5,080,253 | 1/1992 | Zieke . |
| 5,097,950 | 3/1992 | Weiss et al. . |
| 5,108,195 | 4/1992 | Perron . |
| 5,120,138 | 6/1992 | Midgley et al. . |
| 5,148,940 | 9/1992 | Mendise . |

*Primary Examiner*—Allan N. Shoap
*Assistant Examiner*—Stephen Cronin
*Attorney, Agent, or Firm*—Andrus, Sceales, Starke & Sawall

[57] ABSTRACT

A receptacle fox collecting body secretions or medical waste, including an outer rigid open-top container and an inner flexible, transparent bag or liner. The open top of the bag can be closed by a rib and groove type connection that extends the full width of the bag side tabs extend outwardly from opposite sides of the bag and are provided with finger holes. The bag has a size such that the upper portion of the bag drapes downwardly over the upper end of the container and the side tabs are located between the container and the downwardly hanging upper edge portion of the bag. After receiving secretions, the operator grasps the side tabs, pulling upwardly and outwardly to remove the bag from the container. The bag can then be closed through operation of the rib and groove connection.

14 Claims, 1 Drawing Sheet

MULTI-PURPOSE SECRETION RECEPTACLE

BACKGROUND OF THE INVENTION

Because of the prevalence of the HIV virus, there has been increased awareness in the health care industry for the protection of health care personnel. Health care personnel have been urged to use gloves, gowns, goggles and masks to provide a safe work environment when exposed to blood, chemicals, or other potentially infectious or hazardous materials.

One area in which protection of personnel is needed is in the use and handling of receptacles intended to collect gastric and respiratory secretions, or chemotherapeutic agents in emesis.

In the past, emesis basins have been used for receiving and handling of these secretions. The typical emesis basin is kidney-shaped, and is relatively shallow, having a depth of about two inches. Health care personnel are exposed to risk during disposing of secretions from the emesis basin and cleansing the basin, which is intended to be reusable. More specifically, the shallow nature of the typical emesis basin can result in splashing of the secretion as it is deposited in the basin, and if the basin is relatively full, any tilting of the basin during handling can cause spillage. Because of the open nature of the emesis basin, there is increased risk of exposure due to splashing or spilling of the secretion, and during cleaning of the basin.

While the convention emesis basis has embossed graduations indicating the volumetric content, the graduations are difficult to read by health care personnel. As a further disadvantage, the conventional emesis basin has a limited volume of about 500 cc, and in certain cases the volume of the secreted material may overwhelm the capacity of the basin.

It has also been found that in many cases the conventional emesis basin is not properly cleaned, resulting in an unsanitary condition and generating odors. Cleaning of the emesis basin is not only an unpleasant task, but also requires substantial time.

SUMMARY OF THE INVENTION

The invention is directed to a receptacle for collecting body secretions, or other waste material. The receptacle includes an outer rigid, open-top container or vessel, and a flexible transparent disposable bag or liner is located within the container. The open top of the bag can be closed by locking elements, preferably a rib and groove type connection that extends the full width of the bag and provides a seal for the contents of the bag.

Extending outwardly from opposite sides of the bag beneath the rib and groove connection are side tabs, and each side tab is provided with a finger hole. The bag has a size such that the upper end portion of the bag will drape over the upper edge of the container and hang downwardly along the outer surface of the container, with the side tabs being located between the outer surface of the container and the draped portion of the bag.

After secretions are received in the bag, the operator reaches under the draped portion of the bag and grasps the side tabs, and by pulling upwardly and outwardly, the bag is removed from the container without the operator contacting secretions in the bag or secretions that may have spilled or splashed onto the exposed surface of the draped portion of the bag.

In addition, the upper end of the bag is provided with a pair of pull tabs, each of which is located adjacent one of the locking elements. The pull tabs are offset and by pulling laterally or outwardly on the tabs, the bag can be opened to expose the contents.

The plastic bag is preferably formed with longitudinal pleats and in the folded condition, the bag tapers downwardly, so that the lower tapered end of the bag can be readily inserted into the container. The pleated configuration enables the lower end of the bag to conform to the shape of the outer container.

As a feature of the invention, one or more layers of pressure sensitive adhesive can be located on the outer surface of the bag adjacent the open upper end of the bag. The pressure sensitive adhesive is normally covered by a release layer, and by removing the release layer, the outwardly draped portion of the bag can be attached to the outer surface of the container through use of the pressure sensitive adhesive.

The outer container is preferably formed of paperboard and is capable of being collapsed to a generally flat state. It is contemplated that the outer container and bag would be supplied as unit, with the container being folded in the flat condition for shipment and storage, and the bag contained within the folded container.

The invention provides distinct advantages over the emesis basin presently utilized. With the use of the bag there is no contact with secretions. When removing the bag from the container, the operator will reach under the draped over portion of the bag to grasp the side tabs so there is no contact with the inner surface of the bag which may contain secretions. The bag when removed can be immediately closed and sealed, so that it is more aesthetically appealing and there is decreased exposure to odors.

As the bag is transparent, the contents of the bag can be readily examined. The bag preferably contains a series of volumetric graduations, so that the volume of the secretion can be readily ascertained.

It is contemplated that the outer carton or container can be re-used with a fresh bag and, as previously noted, the container is preferably constructed, so that it will fold to a generally flat condition for storage and shipment.

The contents of the bag can either be flushed down the toilet or other suitable drain, or alternately, if the secretions contain hazardous materials, the bag can be sealed and disposed of with other hazardous waste. dr Other objects and advantages will appear in the course of the following description.

DESCRIPTION OF THE DRAWINGS

The drawings illustrate the best mode presently contemplated of carrying out the invention.

In the drawings.

DESCRIPTION OF THE ILLUSTRATED EMBODIMENT

Figure 1:
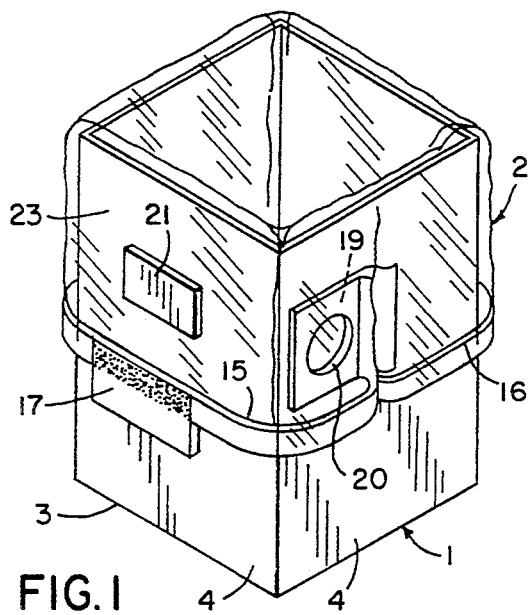
FIG. 1 is a perspective view of the receptacle of the invention.

FIG. 1 shows a receptacle having particular use for receiving and containing body secretions, such as gastric or respiratory secretions. The receptacle includes an outer rigid container or box 1, preferably constructed of paperboard, and a flexible transparent bag or liner 2 is located within the container.

Container 1 includes a generally rectangular bottom wall 3, and side walls 4 extend upwardly from the bottom wall, with the adjacent side edges of the side walls being connected together to provide an open top container.

Figure 4:
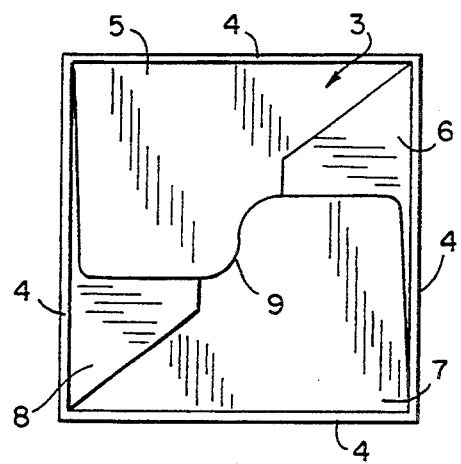
FIG. 4 is a top view of the outer container showing the construction of the container bottom.
Figure 2:
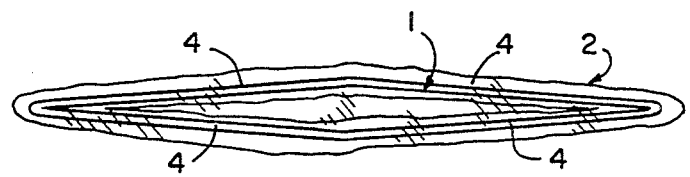
FIG. 2 is a top plan view of the receptacle in the folded condition.

In the preferred form of the invention, container 1 can be collapsed to a generally flat state, as shown in FIG. 2 for ease of shipping and storing. To provide the collapsible nature, bottom wall 3 is formed of four section 5, 6, 7, and 8, each of which is connected to the lower edge of one of the side walls 4. When the container is expanded to the open or rectangular shape, as shown in FIG. 4, the mating edges of section 5 and 7 engage each other, as indicated at 9, to maintain the container in the open condition.

Figure 3:
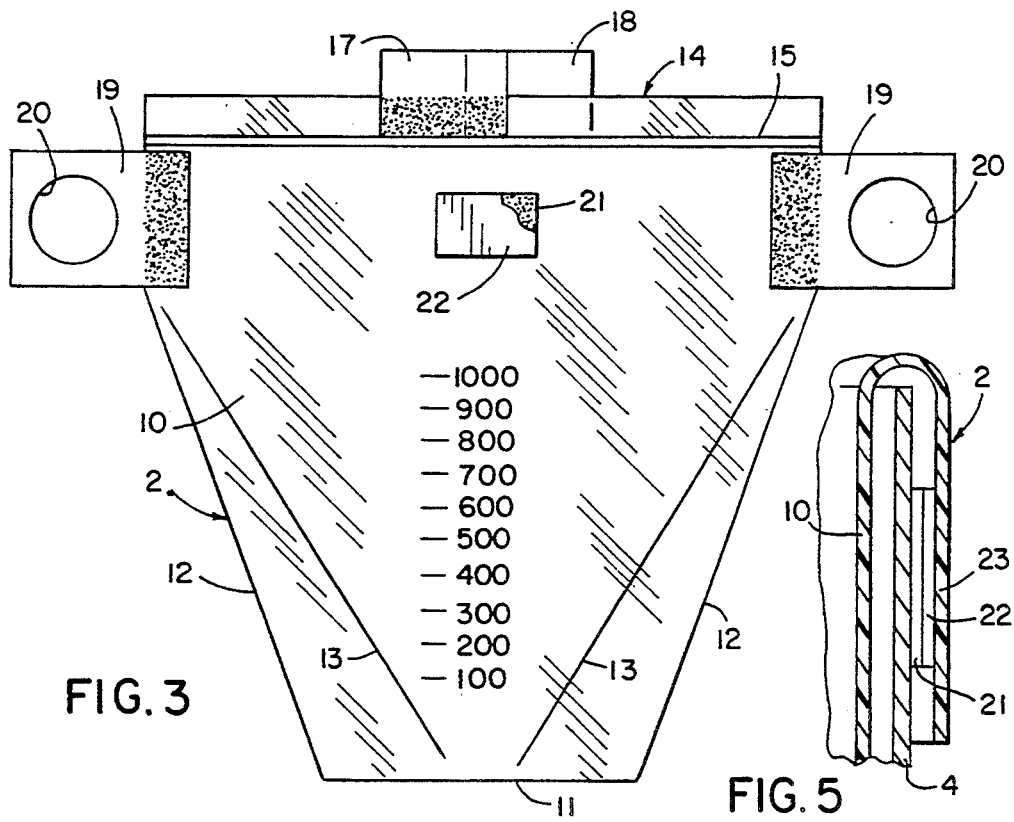
FIG. 3 is a plan view of the bag or liner.

Bag 2 is preferably formed of a pair of panels or sheets 10 formed of transparent plastic material, such as polyethylene. The corresponding bottom edges 11 of the panels 10 are connected together by heat sealing, or the like, and the side edges 12 are also joined together to provide an open top bag. As shown in FIG. 3, pleats 13 are formed in the opposite sides of the bag. The bag 2 tapers downwardly and inwardly which facilitates insertion of the bag within container 1, and the pleated construction enables the lower portion of the bag to expand outwardly to conform to the contour of the container.

The upper edge portions of panels or sheets 10 are adapted to be sealed together by a releasable closure indicated generally by 14. Closure 14 can take the form of a rib and groove type connection, in which the upper edge portion of one of the panels 10 is provided with a rib 15, which can be press fitted and sealed within a groove 16 formed in the upper edge portion of the opposite panel. The closure 14 extends completely across the width of the bag and when engaged, provides a seal for the upper end of the bag.

Pull tabs 17 and 18 are connected to the upper edges of panels 10, and as best shown in FIG. 3, the pull tabs are offset from each other. By grasping the pull tabs 17 and 18, the releasable closure 14 can be opened to expose the contents of the bag.

Mounted on the sides of bag 2, below the closure 14, are side tabs 19. Side tabs 19 are located at the ends of the closure 14 and are preferably colored, so that they are visible through the bag when the bag is inserted in the container and the upper end portion of the bag is draped outwardly over the container. Each side tab 19 is provided with a finger hole 20.

As a feature of the invention, a layer of pressure sensitive adhesive 21 can be applied to one or more areas of the upper portion of bag 2, preferably at a location beneath the closure 14. The adhesive layer 22 is normally covered by a release sheet 22. By removing the release sheet 22, the adhesive layer 21 will be exposed and can be pressed against the outer surface of container 1 to provide an attachment of bag 2 to the container.

Figure 5:
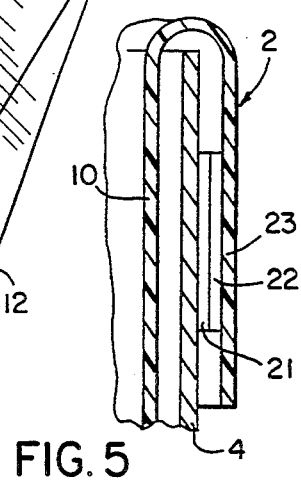
FIG. 5 is a fragmentary vertical section showing the bag being draped over a side wall of the container.

To assemble bag 2 in container 1, closure 14 is opened and the bag is inserted into the container. The length of the bag is substantially greater than the height of the container, so that the upper portion of the bag is draped outwardly over the upper edge of the container, as shown in FIG. 1 and 5. In this position, as shown in FIG. 1, pull tabs 17 an 18 are exposed, while the side tabs 19 are located between the outer surface of the container and the draped over portion 23 of the bag as shown in FIG. 5. If desired, the release layer 72 can be removed from the pressure sensitive adhesive 21, so that the adhesive layer will then secure the upper draped portion 23 of the bag to the outer surface of the container.

After the body secretions have been received within the bag, the operator reaches under the draped portion 23 of the bag and grasps the side tabs 19. As the side tabs are preferably colored, they are readily visible through the plastic bag 2. With the side tabs 19 grasped, the operator then pulls upwardly and outwardly to remove the bag 2 from the container. With the construction of the invention, the operator is completely isolated from any secretions, both within the bag and on the exposed surface of the draped portion 23.

The secretions contained within the bag can then be poured down the toilet, or other drain, and by inserting the fingers of one hand through the finger holes 20 in both of the side tabs 19, the open end of the bag will be formed into a spout-like shape to facilitate pouring of the secretions from the bag. In the event the secretions contains hazardous material, the bag can be sealed by the closure 14 and the bag can then be disposed of with other hazardous waste.

The construction of the invention provides a widemouth, relatively deep receptacle which can be readily set up by folding the collapsed box into the rectangular form. It is contemplated that the outer container or box can be reused with fresh plastic liners.

The receptacle of the invention eliminates contact with body secretions. The side tabs 19 of the bag to be grasped by the operator in removing the bag are located between the draped over portion 23 of the bag, and the outer surface of the container 1, in a location where the side tabs cannot be contacted by any secretion that may have dripped or splashed from the bag.

In the folded or collapsed state, as shown in FIG. 2, the shipment, storage and handling of the receptacle is facilitated.

As the bag is formed of transparent plastic material, the secretions can be readily examined for evidence of blood, or bile, or undigested food particles in the secretion. The volumetric graduations on the bag, enable the attendant to readily determine the volume of the secretions. The bag 2 has a substantial volume, greater than 1,000 cc and, as such, will readily contain the complete quantity of the secretions, so that the secretions will not spill over from the bag and container.

As the bag 2 has a substantial depth and can be fully sealed through the closure 14, the bag containing the secretions can be transported without danger of the secretions being spilled or splashing from the bag.

It is contemplated that the bag 2 can also be used as a suction canister liner in which the lid of the canister is sealed to the draped-over portion of the bag and suitable tubing, or the like, is connected to both the patient and to a source of vacuum, so that secretions can be drawn from the patient to the canister.

The invention can also be used as a bedside receptacle for soiled tissue, toilet paper, and the like.

Various modes of carrying out the invention are contemplated as being within the scope of the following claims particularly pointing out and distinctly claiming the subject matter which is regarded as the invention.

We claim:

1. A medical receptacle, comprising a container having a bottom wall and a side wall and an open upper end, a flexible bag disposed in the container and having an open top, the height of the bag being greater than the height of the container and the upper peripheral portion of the bag being draped over the upper end of the container to provide a draped portion, releasable connecting means for securing opposed portions of the upper end of the bag together to effect a closure of the bag, and a pair of side tabs separate from said releasable connecting means and extending outwardly from the bag at spaced locations on the bag, each side tab having a first end connected to said bag and a second free end, said side tabs being located between the outer surface of the container and said draped portion and being covered by said draped portion whereby the material deposited in the bag will not contact said side tabs.

2. The receptacle of claim 1, wherein the releasable connecting means comprises a first locking element extending the width of the bag and a second locking element extending the width of the bag and engageable with said first locking element.

3. The receptacle of claim 2, wherein said first locking element comprises an elongated rib and said second locking element comprises a groove to receive the rib.

4. The receptacle of claim 2, and including a first pull tab connected to one side of the bag adjacent said first locking element, and a second pull tab connected to the opposite side of the bag adjacent said second locking element.

5. The receptacle of claim 4, wherein said pull tabs are offset from each other.

6. The receptacle of claim 1, wherein said side tabs are located beneath said connecting means.

7. The receptacle of claim 6, wherein each side tab is provided with a finger hole.

8. The receptacle of claim 1, wherein said bag is tapered downwardly and inwardly.

9. The receptacle of claim 1, wherein said bag is composed of transparent material and said tabs are colored, whereby said side tabs are visible through said draped portion of said bag.

10. A receptacle for receiving secretions and medical waste, comprising a substantially rigid container having a bottom wall and a side wall extending up from said bottom wall and an open upper end, a flexible transparent bag disposed in the container and having an open top, the height of the bag being greater than the height of the container whereby the upper peripheral portion of the bag is draped over the upper end of the container to provide a draped portion, releasable connecting means for securing opposed portions of the upper end of the bag together to provide a sealed bag, and a pair of non-elastic side tabs extending outwardly from the bag at spaced locations on the bag, each side tab having a first end connected to said bag and a second free end, said side tabs being located between the outer surface of the container and said draped portion and being completely enclosed by said draped portion whereby material deposited in said bag will not contact said side tabs, each of said side tabs having a finger hole whereby grasping said side tabs by inserting the fingers between said draped portion and the container and thereafter pulling upwardly and outwardly on said side tabs will remove said bag from said container.

11. The receptacle of claim 10, wherein said container is composed of paperboard and is collapsible to a generally flat folded state.

12. The bag construction of claim 10, and including pressure sensitive adhesive means on the outer surface of the bag for attachment of the bag to a container.

13. The bag construction of claim 10, and including a release layer disposed on said adhesive means.

14. The bag construction of claim 10, and including a series of volumetric graduations on the bag indicating the volume of the contents, said graduations being located circumferentially between said pair of side tabs.

* * * * *